United States Patent [19]

Blythin

[11] Patent Number: 4,632,923
[45] Date of Patent: Dec. 30, 1986

[54] SUBSTITUTED HETERO SPIRO PYRIDINE DERIVATIVES AS ANTI-ALLERGY AND ANTI-INFLAMMATORY AGENTS

[75] Inventor: David J. Blythin, North Caldwell, N.J.

[73] Assignee: Schering Corporation, Kenilworth, N.J.

[21] Appl. No.: 641,076

[22] Filed: Aug. 15, 1984

[51] Int. Cl.⁴ .................. A61K 31/495; C07D 513/20
[52] U.S. Cl. .................................. 514/247; 514/248; 514/250; 514/255; 514/278; 546/17; 544/230; 544/231
[58] Field of Search ................. 546/17; 514/278, 266, 514/250, 248, 247, 255; 544/230, 231

[56] References Cited

FOREIGN PATENT DOCUMENTS

| | | | |
|---|---|---|---|
| 0018139 | 10/1980 | European Pat. Off. | ............ 544/279 |
| 0092786 | 11/1983 | European Pat. Off. | ............ 544/349 |
| 2255068 | 7/1975 | France | .................. 546/17 |
| 855022 | 11/1960 | United Kingdom | ............... 546/155 |

OTHER PUBLICATIONS

Kaneko et al., Chem. Pharm. Bull., 17, 1290 (1969).
Fournier et al., Bull. Soc. Chim. Fr., 364 (1968).

*Primary Examiner*—Robert T. Bond
*Attorney, Agent, or Firm*—James R. Nelson; Stephen I. Miller

[57] ABSTRACT

Substituted heterospiro pyridine derivatives are anti-allergic and anti-inflammatory agents. They are also useful for the treatment of peptic ulcers.

Methods for their preparation and use are disclosed.

29 Claims, No Drawings

SUBSTITUTED HETERO SPIRO PYRIDINE DERIVATIVES AS ANTI-ALLERGY AND ANTI-INFLAMMATORY AGENTS

BACKGROUND OF THE INVENTION

The production of a spiro[cyclopentane]-quinolinedione is described in Chem. Pharm. Bull., 17, 1290 (1969). Several additional spiroquinoline diones are disclosed in Bull. Soc. Chim. Fr., 364 (1968). The references do not describe pharmaceutical uses for these compounds.

SUMMARY OF THE INVENTION

The invention sought to be patented in its chemical compound aspect is a compound having the structural formula I:

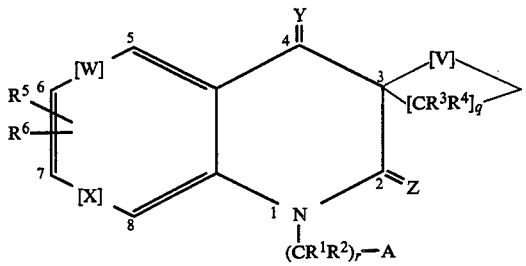

wherein

W and X may be the same or different and are CH or N and are at any of the ring positions 5, 6, 7 or 8;

Y and Z may be the same or different and are O or S;

$R^5$ and $R^6$ may be the same or different and are hydrogen, alkyl having from 1 to 6 carbon atoms, halogen, nitro, alkoxy having from 1 to 6 carbon atoms, trifluoromethyl, alkylthio having 1 to 6 carbon atoms, or cyano;

$R^1$, $R^2$, $R^3$ and $R^4$ are independently hydrogen, alkyl having 1 to 6 carbon atoms, $CH_2OH$, $CO_2R^7$ [wherein $R^7$ is hydrogen or alkyl having 1 to 6 carbon atoms] or hydroxy;

V is oxygen, $S(O)_n$ [wherein n is 0, 1 or 2], N—$R^8$ [wherein $R^8$ is hydrogen, alkyl having from 1 to 6 carbon atoms, carboxylic acyl having from 1 to 7 carbon atoms, sulfonylalkyl having from 1 to 6 carbon atoms, carboalkoxy having from 2 to 7 carbon atoms, $CONH_2$, phenyl, pyridyl of which the last two may be substituted with up to three of any of the following substituents, Q: hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_n$—$R^a$ [wherein n is defined herein and $R^a$ is alkyl having from 1 to 6 carbon atoms], $NHSO_2R^a$ [wherein $R^a$ is defined herein], $NHSO_2CF_3$, $NHCOCF_3$, $SO_2NH_2$, $COR^b$ [wherein $R^b$ is OH, NH—$R^a$ or $OR^a$ (wherein $R^a$ is defined herein)], O—B—$COR^b$ [wherein B is alkylene having from 1 to 4 carbon atoms and $R^b$ is defined herein], or $NHCOR^c$ [wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having 1 to 6 carbon atoms)];

r is 0, 1 or 2;

q is an integer of from 2 to 6; and

A is phenyl, naphthyl, indenyl, indanyl, pyridyl, pyrimidyl, pyrazinyl, furyl, thienyl, imidazolyl, thiazolyl or oxazolyl any of which may be substituted with up to three substituents, Q as defined herein.

A preferred subgenus of compounds is that wherein Y and Z are both oxygen.

An additional preferred subgenus of compounds is represented by the structural formula II:

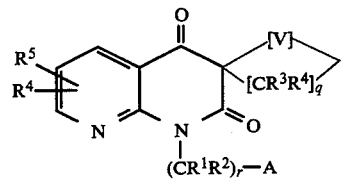

wherein $R^1$, $R^2$, $R^3$, $R^4$, $R^5$, $R^6$, A, r and q are defined herein.

An additional preferred subgenus of compounds is represented by the structural formula III:

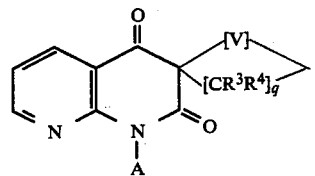

wherein $R^3$, $R^4$, V, A, and q are defined herein.

A further additional preferred subgenus of compounds is represented by the structural formula III wherein $R^3$, $R^4$, A and q are defined herein and V is oxygen.

The invention sought to be patented in its pharmaceutical composition aspect is a pharmaceutical composition which comprises a compound having structural formula I in combination with a pharmaceutically acceptable carrier.

The invention sought to be patented in a first pharmaceutical method aspect is a method for treating allergic reactions in a mammal which comprises administering an anti-allergic effective amount of the above-defined pharmaceutical composition to said mammal.

The invention sought to be patented in a second pharmaceutical method aspect is a method for treating inflammation in a mammal which comprises administering an anti-inflammatory effective amount of the above-defined pharmaceutical composition to said mammal.

The invention sought to be patented in a third pharmaceutical method aspect is a method for treating peptic ulcers in a mammal which comprises administering a cytoprotective effective amount of the above defined pharmaceutical composition to said mammal.

DESCRIPTION OF THE INVENTION

The compounds of the invention may be prepared from a properly substituted compound having the structural formula IV

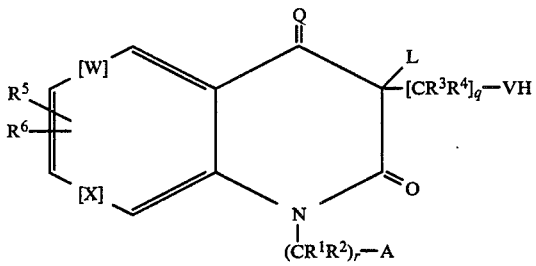

wherein W, X, $R^1$, $R^2$, $R^3$, $R^4$, $R^5$, $R^6$, V, A, r and q are defined herein, and L is a substituent known to those skilled in the art as a "leaving group."

Treatment of compound IV with an organic base such as triethylamine or 1,8-diazabicyclo [5.4.0] undec7-ene, DBU [Angew. Chem., Internat. Ed., 6 76 (1967)] in a nonreactive solvent such as chloroform will produce the compounds of the invention having structural formula I, wherein Y and Z are both oxygen.

For purposes of the invention a "leaving group" is defined as a substituent which may be displaced and carry a negative charge. Examples of such substituents are the bromide and iodide anions. The preferred leaving group is the bromide anion.

Compounds having structural formula IV wherein L is bromine and VH is hydroxy may be prepared by treatment of the corresponding non-brominated compounds with a solution of bromine in chloroform. Other compounds having structural formula IV wherein leaving group substituent L is iodine and VH is hydroxy may be prepared by methods known to those of skill in the art.

The compounds having structural formula IV without the leaving group substituent L may be prepared by known methods from known starting materials. Such methods are described, for example, in preparative examples 1, 2, 4 and 6 herein.

Exemplary of such starting materials for preparing compounds having structural formula IV without leaving group substituent L are 2-anilino nicotinic acids which may be prepared, for example, as described in U.S. Pat. No. Re. 26,655; and 2-phenylamino-3-pyrazine carboxylate esters which may be prepared substantially as exemplified herein starting with a 2-amino-3-pyrazine carboxylate ester. 2-Anilino-3-pyrazine carboxylic acid is a known compound, C.A., 75, 20154e (1971), which may be esterified by standard procedures.

The compounds having structural formula I wherein Y and/or Z are oxygen may be converted to the corresponding compounds wherein Y and/or Z are sulfur by known methods. For example treatment with Lawesson's Reagent [2,4-bis(4-methoxyphenyl)-1,3-dithia-2,4-diphosphetane-2,4-disulfide] in hot toluene will effect this conversion.

When utilized herein and in the appended claims the below listed terms, unless specified otherwise, are defined as follows:

halogen—fluorine, chlorine, bromine and iodine;
alkyl and alkoxy—comprised of straight and branched carbon chains containing from 1 to 6 carbon atoms;
alkenyloxy—comprised of straight and branched carbon chains containing from 3 to 6 carbon atoms and comprising a carbon to carbon double bond; and
alkynyloxy—comprised of straight and branched carbon chains containing from 3 to 6 carbon atoms and comprising a carbon to carbon triple bond.

The compounds of the invention include a —$(CR^1R^2)_r$— substituent wherein the $R^1$ and $R^2$ groups may vary independently. Thus, for example, when r equals 2 the following patterns of substitution (wherein hydrogen and $CH_3$ are used to represent any substituent, $R^1$ or $R^2$,) are contemplated: —$C(CH_3)_2CH_2$—, —$CH_2C(CH_3)_2$—, —$CH_2CH(CH_3)$—, —$CH(CH_3)CH_2$—, —$(C(CH_3)H)_2$— and homologues thereof. In addition when r equals 2, substituents such as —$C(CH_3)_2CH(C_2H_5)$—, —$CH(CH_3)CH(C_2H_5)$—, —$CH(i—C_3H_7)CH(C_2H_5)$— are also contemplated.

The compounds of the invention include a —$(CR^1R^2)_r$— substituent. It would be obvious to one of ordinary skill in the art that due to problems of stability there are limitations involving the $R^1$ and $R^2$ groups. One limitation is that neither the $R^1$ nor $R^2$ group can be a hydroxy group attached to the carbon alpha to the ring nitrogen. Another limitation is that the $R^1$ and $R^2$ groups cannot both be hydroxy groups. In the event that r equals zero, substituents indicated by A are attached directly to the ring nitrogen.

The compounds of the invention include a —$(CR^3R^4)_q$— substituent wherein the $R^3$ and $R^4$ groups may vary independently. Thus, for example, when q equals 2 the following patterns of substitution (wherein hydrogen and $CH_3$ are used to represent any substituent, $R^3$ or $R^4$,) are contemplated: —$C(CH_3)_2CH_2$—, —$CH_2C(CH_3)_2$—, —$CH_2CH(CH_3)$—, $CH(CH_3)CH_2$—, —$(C(CH_3)H)_2$—, and homologues thereof. In addition when q equals 2, substitutents such as —$C(CH_3)_2CH(C_2H_5)$—, —$CH(CH_3)CH(C_2H_5)$—, —$CH(i—C_3H_7)CH(C_2H_5)$— are also contemplated.

The compounds of the invention include a —$(CR^3R^4)_q$— substituent. It would be obvious to one of ordinary skill in the art that due to problems of stability there are limitations involving the $R^3$ and $R^4$ groups. One limitation is that neither the $R^3$ nor $R^4$ group can be a hydroxy group attached to the carbon alpha to the ring heteroatom. Another limitation is that the $R^3$ and $R^4$ groups cannot both be hydroxy groups.

Certain compounds of the invention may exist in isomeric forms. The invention contemplates all such isomers both in pure form and in admixture, including racemic mixtures.

In structural formulas I, II and III herein, substituent V which represents the hetero atom in the spiro ring is attached directly to the spiro carbon atom, i.e. the carbon atom identified as number 3 in structural formula I.

The compounds of the invention of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

The compounds of this invention can be used to treat allergy caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy method of this invention is identified by tests which measure a compound's inhibition of anaphylactic bronchospasm in sensitized guinea pigs having antigen induced broncho-constriction. For example, the compound 1-phenyl-3',4',5',6'-tetrahydro-spiro[1,8-naphthyridine 3,2'-(2H)pyran]-2,4-dione was found to inhibit anaphylactic bronchospasms in such test procedure when given at an oral dose of 5 mg/kg. Said compound was also found to inhibit allergen-induced histamine release from guinea pig and human sensitized tissue. The compounds are effective non-adrenergic, non-anticholinergic antianaphylactic agents. When administered orally they are active at doses from about 0.1 to 50 mg/kg of body weight; when administered parenterally, e.g., intravenously, the compounds are active at dosages of from about 0.01 to 5 mg/kg body weight, when administered by inhalation (aerosol or nebulizer) the compounds are active at dosages of about 0.1 to 5 mg per puff, one to four puffs may be taken every 4 hours.

The compounds of this invention are also useful for the treatment of inflammation; thus, they are useful for the treatment of: arthritis, bursitis, tendonitis, gout and other inflammatory conditions. The anti-inflammatory use of the compounds of the present invention may be demonstrated by the Reversed Passive Arthus Response technique as set forth below using male Lewis inbred albino rats (Charles River) weighing 180-200 grams. The potency of the compounds is determined using indomethacin as the standard. On the basis of the test results, a dosage range of 5 mpk to about 50 mpk in divided doses taken at about 4 hour intervals is recommended.

The dosage to be administered and the route of administration depends upon the particular compound used, the age and general health of the patient and the severity of the inflammatory condition. Thus, the dose ultimately decided upon must be left to the judgment of a trained health-care practitioner.

Reversed Passive Arthus Response (RPAR) Animals, Materials and Methods

Male Lewis inbred albino rats weighing 180-200 grams obtained from Charles River Breeding Laboratories are used in these experiments. The rats are housed 3 animals/cage and food and water are allowed ad libitum. The animals are numbered 1-3 in each cage and color marked for identification purposes.

Drug and Reagent Preparation

All reagents and drugs are prepared just prior to the study. Crystallized and lyophilized bovine serum albumin (BSA), obtained from Sigma Chemical Company, is solubilized without shaking in cold sterile pyrogen free saline (10 mg/ml). Lyophilized anti-bovine serum albumin (IGG fraction), obtained from Cappel Laboratories, is suspended in sterile distilled water and diluted with cold pyrogen free saline (PFS) just prior to use. The final concentration of anti-bovine serum albumin is 0.5. mg/ml of PFS. Both BSA and anti-BSA solutions are iced during use. Drugs are suspended or solubilized in an aqueous solution of methyl cellulose (MC) with a homogenizer just prior to administration.

Drug Administration and Induction of Inflammation

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after the last dose the animals are lightly anesthetized with ether and "sensitized" by injection into the penile vein with 0.2 ml of PFS containing 1.0 mg of BSA. One hour later, the animals are "challenged" in the right rear paw with subplantar injections of 0.2. ml of PFS containing 0.1 mg of anti-BSA. Immediately after the subplantar injection, the right paw is dipped (up to the lateral maleolus) into the mercury well of a plethysmograph. The volume of mercury displaced is converted to weight and recorded. This value is considered to be the control reading for the animal. Paw volumes are also recorded with a plethysmograph during the development of the inflammation at 2 and 4 hours post-challenge.

Results

Results are expressed by the change in paw volume ($\Delta$ paw volume) from the control reading for each animal to that recorded 2 and 4 hours post-challenge. All drug treated groups are compared to the MC control for significant differences with an analysis of variance. Differences from control in drug-treated groups are expressed as percent change from control.

The compounds of this invention are also useful in the treatment of peptic ulcers. They display chemotherapeutic activity which enables them to relieve the symptoms of peptic ulcer disease, stress ulceration, and promote healing of gastric and/or duodenal ulcers. The antiulcer activity of the compounds of this invention is identified by tests which measure the cytoprotective effect in rats. The compounds are also useful as conjunctive therapeutic agents for coadministration with such antiinflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents.

The compounds of this invention are evaluated for their antiulcer activity characteristics by standard biological testing procedures.

In cytoprotective tests in rats in which ethanol is employed to induce gastrointestinal damage, the compounds of this invention are found to be effective at doses of about 0.5-50 mg/kg of body weight per day. Preferably the total dosages are administered in divided doses per day.

When administered parenterally, e.g. intravenously, the compounds are administered at a dosage range of about 0.05-5 mg/kg of body weight in single or multiple daily doses.

To treat peptic ulcer disease, and prevent and treat drug-induced gastric ulceration, the active compounds of this invention can be administered in unit dosage forms such as tablets, capsules, pills, powders, granules, sterile parenteral solutions or suspensions, suppositories, mechanical delivery devices, e.g. transdermal, and the like.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

PREPARATIVE EXAMPLE 1

4-Hydroxy-3-(4-hydroxybutyl)-1-phenyl-1,8-naphthyridin-2(1H)-one

A mixture of methyl 2-phenylamino-nicotinate (100 g.), epsilon-caprolactone (1000 g.) and potassium t-butoxide (200 g.) was stirred at room temperature, in a nitrogen atmosphere, for ½ hr. It was heated at 45° C. for 1 hr. then at 85° C. for 2 hrs. and finally at 105° C. for 3 hr.

The hot mixture was poured carefully into 8 L of 5% KOH solution and was stirred overnight.

The mixture was extracted with 2 L of ether and the aqueous phase was retained. It was extracted again with a fresh 2 L of ether. The clear aqueous phase was adjusted to pH 4.5 with conc. HCl to yield a white solid which was filtered off, washed with water and dried to yield 4-hydroxy-3-(4-hydroxybutyl)-1-phenyl-1,8-naphthyridin-2(1H)-one, m.p. 205.5°-206.5° C. (from isopropanol).

By substituting the relevant ester and lactone in this preparative example intermediates to other compounds of the invention may be prepared.

PREPARATIVE EXAMPLE 2

4-Hydroxy-3-(3-hydroxypropyl)-1-phenyl-1,8-naphthyridin-2(1H)one

Methyl 2-phenylamino-nicotinate (25 g.) was dissolved in delta-valerolactone (240 g.) with stirring in an atmosphere of nitrogen. To the resulting solution was added potassium t-butoxide (50 g.) and the mixture was stirred at room temperature for ½ hr. It was then heated to 100° C. for 3 hr. after which time it was poured into 1 L of 5% NaOH solution and stirred overnight.

The mixture was extracted (2×) with 1 L of ether then the aqueous layer was adjusted to pH 4.5 with conc. HCl. The solid which separated was filtered off, washed with water and dried to yield 4-hydroxy-3-(3-hydroxypropyl)-1-phenyl-1,8-naphthyridin-2(1H)-one, m.p. 218°-220° C.

By utilizing the correspondingly substituted starting materials in the procedures of preparative examples 1 or 2, the following compounds were obtained: 1-(4-chlorophenyl)-4-hydroxy-3-(3-hydroxypropyl)-1,8-naphthyridin-2(1H)one, m.p. 249.5°–251° C.;
4-hydroxy-3-(3-hydroxypropyl)-1-(4-metylphenyl)-1,8-naphthyridin-2(1H)one, m.p. 227°–228° C.;
4-hydroxy-3-(3-hydroxypropyl)-1-(4-methoxyphenyl)-1,8-naphthyridin-2(1H)one, m.p. 229°–231° C.;
1-(3,4-dichlorophenyl)-4-hydroxy-3-(3-hydroxypropyl)-1,8-naphthyridin-2(1H)one, m.p. 230°–232° C.;
1-(4-chlorophenyl)-4-hydroxy-3-(4-hydroxybutyl)-1,8-naphthyridin-2(1H)one, m.p. 238°–240° C.;
4-hydroxy-3-(4-hydroxybutyl)-1-(4-methylphenyl)-1,8-naphthyridin-2(1H)one, m.p. 186°–188° C.;
4-hydroxy-3-(4-hydroxybutyl)-1-(4-methoxyphenyl)-1,8-naphthyridin-2(1H)one, m.p. 237°–239° C.;
1-(3,4-dichlorophenyl)-4-hydroxy-3-(4-hydroxybutyl)-1,8-naphthyridin-2(1H)one, m.p. 188°–190° C.;
1-(3-chlorophenyl)-4-hydroxy-3-(4-hydroxybutyl)-1,8-naphthyridin-2-(1H)one, m.p. 176°–178° C.;
4-hydroxy-3-(4-hydroxybutyl)-1-(3-methoxyphenyl)-[1,8]-naphthyridin-2(1H)-one, m.p. 217°–219° C.;
4-hydroxy-3-(4-hydroxybutyl)-1-phenyl-quinolin-2(1H)-one, m.p. 156.5°–158° C.

PREPARATIVE EXAMPLE 3

Ethyl 5-(4-hydroxy-2-oxo-1-phenyl-1H-[1,8]naphthyridin-3-yl)pentanoate

Methyl 2-phenylaminonicotinate (8.5 g.) was dissolved with stirring in diethyl pimelate (80 ml.) in an atmosphere of nitrogen. To the mixture was added potassium t-butoxide (13 g.) and the mixture was stirred at room temperature for 1 hr. It was then heated to 135°–140° C. for 6 hours after which time it was poured into water. The aqueous layer was extracted with methylene chloride and then adjusted to pH 4.5 with conc. HCl. Solid sodium chloride was added after which the solid was filtered off, washed with water and dried, m.p. 168°–169° C.

By substituting diethyl suberate for diethylpimelate in the above procedure; ethyl 6-(4-hydroxy-2-oxo-1-phenyl-1H-[1,8]naphthyridin-3-yl)-hexanoate, m.p. 167°–168° C. was obtained.

PREPARATIVE EXAMPLE 4

4-Hydroxy-3-(5-hydroxypentyl)-1-phenyl-1,8-naphthyridin-2(1H)one

To a suspension of ethyl 5-(4-hydroxy-2-oxo-1-phenyl-1H-[1,8]-naphthyridin-3-yl)pentanoate (1 g.) (prepared as in preparative example 3) in dry dioxane (50 ml.) in an atmosphere of nitrogen is added lithium borohydride (0.34 g.). The mixture is stirred at room temperature for 20 min. then it is heated to 60° C. for 16 hrs.

The product is poured into water, adjusted to pH 4.5 with acetic acid and the resulting solid is filtered off. The solid is washed with water and dried to yield 4-hydroxy-3-(5-hydroxypentyl)-1-phenyl-1,8-naphthyridin-2-(1H)-one.

PREPARATIVE EXAMPLE 5

Methyl-2-phenylamino-3-pyrazine carboxylate (A) Methyl 2-bromo-3-pyrazine carboxylate To a stirred mixture of 12.7 g. of methyl 2-amino pyrazine carboxylate and 47 ml. of 48% hydrobromic acid there was added, dropwise, 12.6 ml. of bromine keeping the temperature at 0°. A solution of 14.4 g. of sodium nitrite in 60 ml. of water was then added, dropwise, at 0° and the reaction mixture stirred for 15 minutes. The reaction mixture was basified to pH 8 with sodium bicarbonate and extracted with ethyl acetate and again with chloroform. The organic layers were dried over magnesium sulfate, filtered and concentrated to a yellow oil. Recrystallization from ether-hexane yielded the product, m.p. 43°–45° C.

(B) Methyl 2-phenylamino-3-pyrazine carboxylate

A mixture of 9.5 g. of methyl 2-bromo-3-pyrazine carboxylate, 8.2 g. of aniline, 0.5 g. of p-toluene sulfonic acid and 100 ml. of water was stirred and refluxed for two hours. The reaction mixture was poured on ice, extracted with ethyl acetate, the organic extracts were dried and concentrated to yield an oil. The crude residue was eluted on a silica gel column with ethyl acetate-hexane (1:2) yielding the product of this example as a yellow solid, m.p. 72°–75° C.

PREPARATIVE EXAMPLE 6

3-(2-Hydroxyethyl)-4-hydroxy-1-phenyl-1,8-naphthyridin-2(1H)one

To a solution of 6.8 g. of methyl 2-phenylamino-3-pyridine carboxylate in 60 ml. of gamma-butyrolactone there was added, under nitrogen, 13.4 g. of potassium tertiary butoxide. The reaction mixture was heated and stirred for one hour at 95° C., poured on ice and stirred overnight. The mixture was extracted with ether, the aqueous layer acidified with acetic acid to pH 4.5 and the product was collected by filtration. Recrystallization from chloroform, acetone, isopropanol yielded the product of this example as a colorless solid; m.p. 235°–236° C.

EXAMPLE 1

1-Phenyl-3',4',5',6'-tetrahydro-spiro-[1,8-naphthyridine-3,2'-(2H)pyran]-2,4-dione A suspension of 4-Hydroxy-3-(4-hydroxybutyl)-1-phenyl-(1,8)-naphthyridin-2(1H)-one (2 g.) in chloroform was stirred in an ice-bath. A solution of bromine (1 g.) in chloroform was added dropwise and the mixture was stirred overnight at room temperature. To this mixture was added a solution of 1,8-diazabicyclo[5.4.0]undec-7-ene (2 g) in chloroform at room temperature. After about ¾ hr. water was added and the pH was adjusted to be slightly acidic. The chloroform layer was separated and washed with saturated NaCl solution. The solution was dried and evaporated to a solid which was washed with ethanol/water and dried to yield 1-phenyl-3', 4', 5', 6'-tetrahydro-spiro[1,8-naphthyridine-3,2'-(2H) pyran]-2,4-dione, m.p. 213°–215° C.

EXAMPLE 2

1-(3-Methoxyphenyl)-3',4',5',6'-tetrahydrospiro[1,8-naphthyridine-3,2'-(2H)pyran]-2,4-dione.

To a suspension of 4-Hydroxy-3-(4-hydroxybutyl)-1-(3-methoxyphenyl)(1,8)-naphthyridin-2(1H)-one (1 g.)in methylene chloride (10 ml),in an ice-acetone bath was added a solution of bromine (0.5 g.) in methylene chloride (5 ml.) over a period of 15 min. The resulting yellow-orange suspension was stirred overnight at room temperature. To the resulting clear yellow solution was added a solution of 1,8-diazabicyclo[5.4.0]undec-7-ene (1 g.), in methylene chloride (5 ml) during 5 mins. The mixture was stirred at room temperature for 3 hrs after which time water (5 ml) was added. The organic layer was separated, dried and evaporated. To the residue was added 50% aqueous ethanol (10 ml.) and after some time the solid was filtered off and recrystallized from isopropanol to yield 1-(3-methoxyphenyl)-3′, 4′, 5′, 6′-tetrahydrospiro[1,8-naphthyridine-3,2′-(2H)pyran]-2, 4-dione, m.p. 181°–183° C.

By utilizing the appropriately substituted starting materials in the above-described procedure, the following products were obtained:

4,5-dihydro-1′-phenyl-spiro [furan-2(3H), 3′(2′H) (1,8) naphthyridine]-2′, 4′(1′H)-dione, m.p. 241.5°–243°° C.; 1-phenyl-spiro(1,8-naphthyridine-3,2′-oxetane)-2, 4-dione, m.p. 233°–235.5° C.; 1-(3-chlorophenyl)-3′, 4′, 5′, 6′,-tetrahydrospiro[1,8-naphthyridine-3, 2′(2H) pyran]-2,4-dione, m.p. 158.5°–160° C.

EXAMPLE 3

1′-Ethoxycarbonyl-1-phenyl-spiro[1,8-naphthyridine 3,2′-piperidine]-2,4-dione (A)

N,2-Bis(ethoxycarbonyl)-2-(3-[2-chloronicotinoyl])-piperidine

A slight excess of 1M-lithium bis(trimethylsilyl)amide in tetrahydrofuran (THF) is cooled in a nitrogen atmosphere to below −60° C. To this is added a solution of ethyl N-ethoxycarbonyl pipecolinate (0.11M) in dry THF, dropwise.

Allow to stand for 2 hr. Then add a solution of ethyl 2-chloronicotinate (0.1M) in dry THF, dropwise.

Allow to stand at −70° C. for at least 4 hrs. Then warm gradually to room temperature. When no starting material remains, add acetic acid and water, and evaporate off the THF.

Isolate the product by extraction and purify by column chromatography.

(B)

N-Ethoxycarbonyl-2-(3-[2-chloro-nicotinoyl])-pipecolinoyl anilide

Carefully hydrolyze the product from part A using excess dilute NaOH in H$_2$OEtOH. Follow by thin layer chromatography (TLC). When no starting material remains, adjust the pH to ca 9 with dil HCl and evaporate to low volume under reduced pressure. To the residue suspended in benzene, add an excess of oxalyl chloride, and warm the mixture until a reaction occurs.

When the reaction is complete evaporate off as much solvent and excess reagent as possible. Then add aniline (2.2 equivs.) in dry THF. Warm to complete the reaction. Then isolate the product by adding water and acetic acid, evaporating off the THF and extracting into CH$_2$Cl$_2$. The product is purified by column chromatography.

(C)

1′-Ethoxycarbonyl-1-phenyl-spiro(1,8-naphthyridine-3,2′-piperidine]-2,4-dione

To a slight excess of 1M-lithium bis(trimethylsilyl)amide in THF, under nitrogen, at −70° C., is added the product from part B, in dry THF, dropwise. After standing for 2hr. at −70° C. the mixture is allowed to warm gradually in ca. 20° C. steps to room temperature. The reaction is followed by TLC at each step. When the reaction is complete, the product is isolated by addition of acetic acid and water. Removal of the THF, and extraction into CH$_2$Cl$_2$ is performed, and the product is purified by column chromatography.

Removal of the carbamate protecting group and subsequent modification of the resulting secondary amine are implemented by standard means well known to one skilled in the art.

I claim:

1. A compound having the structural formula I:

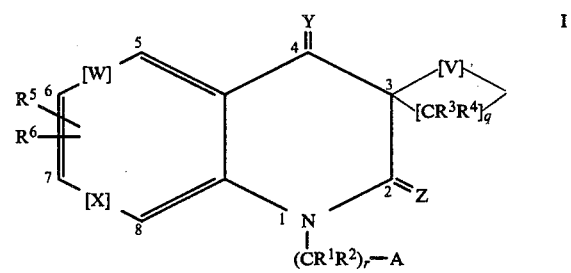

wherein

X and W both represent N;

Y and Z may be the same or different and are O or S;

R$^5$ and R$^6$ may be the same of different and are hydrogen, alkyl having from 1 to 6 carbon atoms, halo, nitro, alkoxy having from 1 to 6 carbon atoms trifluoromethyl, alkylthio having 1 to 6 carbon atoms or cyano;

R$^1$, R$^2$, R$^3$ and R$^4$ are independently hydrogen, alkyl having 1 to 6 carbon atoms, CH$_2$OH, CO$_2$R$^7$ {wherein R$^7$ is hyrogen or alkyl having 1 to 6 carbon atoms} or hydroxy; provided that only one group on any carbon atom can be —OH and such carbon atom is not adjacent to a heteroatom;

V is oxygen, S(O)$_n$ {wherein n is 0, 1 or 2}, N—R$^8$, {wherein R$^8$ is hydrogen, alkyl having from 1 to 6 carbon atoms, carboxylic acyl having from 2 to 7 carbon atoms, sulfonylalkyl having from 1 to 6 carbon atoms, carboalkoxy having from 2 to 7 carbon atoms, CONH$_2$, phenyl, pyridyl of which the last two may be substituted with up to three of any of the following substituents, Q: hydroxy, alkyl having from 1 to 6 carbon atoms, halo, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, S(O)$_n$R$^a$ {wherein n is defined herein an R$^a$ is alkyl having from 1 to 6 carbon atoms}, NHSO$_2$R$^a$ {wherein R$^a$ is defined herein}, NHSO$_2$CF$_3$, NHCOCF$_3$, SO$_2$NH$_2$, COR$^b$ {wherein R$^b$ is OH, NH$_2$ or OR$^a$ {wherein R$^a$ is defined herein)}, O—B-COR$^b$ {wherein B is alkylene having from 1 to 4 carbon atoms and R$^b$ is defined herein}, or NHCOR$^c$ {wherein R$^c$ is hydrogen, alkyl having from 1 to 6 carbon atoms, COR$^d$ (wherein R$^d$ is hydroxy or alkoxy having from 1 to 6 carbon atoms) or NHR$^e$ (wherein R$^e$ is hydrogen or alkyl having from 1 to 6 carbon atoms)}};

r is 0, 1 or 2;

q is an integer of from 2 to 6; and

A is phenyl, naphthyl, indenyl, indanyl, pyridyl, pyrimidyl, pyrazinyl, furyl, thienyl, imdiazolyl, thiazolyl or oxazolyl any of which may be substituted with up to three substituents, Q as defined herein.

2. The compound defined in claim 1 wherein Y and Z are both oxygen.

3. The compound defined in claim 2 wherein r is zero.

4. The compound defined in claim 3 wherein $R^5$ and $R^6$ are both hydrogen.

5. The compound defined in claim 1 wherein W and X are both N at the 5- and 8- position.

6. The compound defined in claim 1 wherein W is situated in the 5- or 8- position.

7. The compound defined in claim 1 wherein q is 3, 4, or 5.

8. The compound defined in claim 7 wherein up to 4 of $R^3$ and $R^4$ are alkyl having 1 to 4 carbon atoms.

9. The compound defined in claim 7 wherein up to 2 of $R^3$ and $R^4$ are alkyl having 1 or 2 carbon atoms.

10. The compound defined in claim 7 wherein q is 3, 4 or 5 and $R^3$ and $R^4$ are hydrogen.

11. The compound defined in claim 10 wherein A is phenyl.

12. The compound defined in claim 11 wherein phenyl is substituted with one or two Q substituents.

13. A compound having the structural formula Ia:

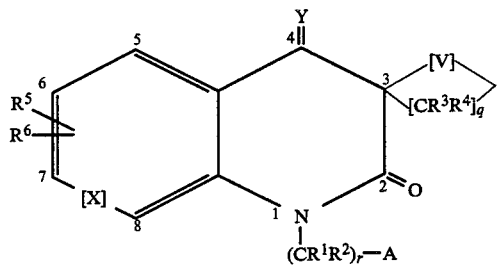

wherein

X represents N;

Y and Z may be the same or different and are O or S;

$R^5$ and $R^6$ may be the same or different and are hydrogen, alkyl having from 1 to 6 carbon atoms, halo, nitro, alkoxy having from 1 to 6 carbon atoms, trifluoromethyl, alkylthio having 1 to 6 carbon atoms or cyano;

$R^1$, $R^2$, $R^3$ and $R^4$ are each independently selected from hydrogen, alkyl having 1 to 6 carbon atoms, $CH_2OH$, $CO_2R^7$ {wherein $R^7$ is hyrogen or alkyl having 1 to 6 carbon atoms} or hydroxy; provided that only one group on any carbon atom can be —OH and such carbon atom is not adjacent to a heteroatom;

V is oxygen, $S(O)_n$ {wherein n is 0, 1 or 2}, N—$R^8$ {wherein $R^8$ is hydrogen, alkyl having from 1 to 6 carbon atoms, carboxylic acyl having from 2 to 7 carbon atoms, sulfonylalkyl having from 1 to 6 carbon atoms, carboalkoxy having from 2 to 7 carbon atoms, $CONH_2$, phenyl, pyridyl of which the last two may be substituted with up to three of any of the following substituents, Q: hydroxy, alkyl having from 1 to 6 carbon atoms, halo, nitro, alkoxy having from 1 to 6 carbon atoms, trifluoromethyl, cyano, cycloalkyl having from 3 to 7 carbon atoms, alkenyloxy having from 3 to 6 atoms, alknyloxy having from 3 to 6 carbon atoms, $S(O)_n$—$R^a$ {wherein n is defined herein and $R^a$ is alkyl having from 1 to 6 carbon atoms}, $NHSO_2R^a$ {wherein $R^a$ is defined herein}, $NHSO_2CF_3$, $NHCOCF_3$, $SO_2NH_2$, $COR^b$ {wherein $R^b$ is OH, $NH_2$ or $OR^a$ {wherein $R^a$ is defined herein)}, O—B—$COR^b$ {wherein B is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy and alkoxy having from 1 to 6 carbon atoms) or $NHR^e$ (wherein $R^e$ is hydrogen or alkyl having 1 to 6 carbon atoms)}};

r is 0, 1 or 2;

q is an integer of from 2 to 6; and

A is phenyl, naphthyl, indenyl, indanyl, pyridyl, pyrimidyl, pyrazinyl, furyl, thienyl, imidazolyl, thiazolyl or oxazolyl any of which may be substituted with up to three substituents, Q as defined herein.

14. A compound having the structural formula II

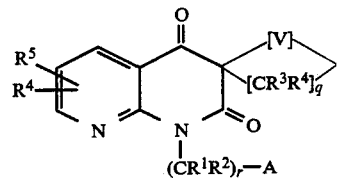

wherein $R^1$, $R^2$, $R^3$, $R^4$, $R^5$, $R^6$, A, V, r and q are as defined in claim 13.

15. A compound having the structural formula III

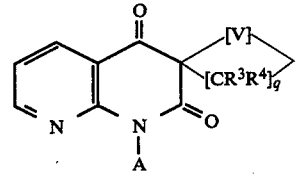

wherein $R^3$, $R^4$, V, A and q are as defined in claim 13.

16. 1-phenyl-3', 4', 5', 6'-tetrahydro-spiro[1,8-naphthyridine-3,2'-(2H)pyran]-2,4-dione.

17. The compounds having the names:

1-phenyl-3', 4', 5', 6'-tetrahydro-spiro[1,8-naphthyridine-3,2'-(2H)pyran]-2,4-dione;

1-(3-methoxyphenyl)-3', 4', 5', 6'-tetrahydro-spiro[1,8-naphthyridine-3,2'-(2H)pyran]-2,4-dione;

4,5-dihydro-1'-phenyl-spiro[furan-2(3H), 3'(2'H) (1,8)naphthyridine]-2',4'(1'H)-dione;

1-phenyl-spiro[1,8-naphthyridine-3,2'-oxetane]-2,4-dione; and 1-(3-chlorophenyl)-3',4',5',6'-tetrahydro-spiro[1,8-naphthyridine-3,2'-(2H)pyran]-2,4-dione.

18. A pharmaceutical composition for treating allergic reactions which comprises a compound having structural formula I as defined in claim 1 in combination with a pharmaceutically acceptable carrier.

19. A method for treating allergic reactions in a mammal which comprises administering an anti-allergic effective amount of a pharmaceutical composition comprising a compound having a structure according to formula Ia, as defined in claim 13, in combination with a pharmaceutically acceptable carrier to said mammal.

20. A method for treating inflammation in a mammal which comprises administering an anti-inflammatory effective amount of a pharmaceutical composition comprising a compound having a structure according to formula Ia, as defined in claim 13, in combination with a pharmaceutically acceptable carrier to said mammal.

21. A method for treating peptic ulcers in a mammal which comprises administering a cytoprotective effective amount of a pharmaceutical composition comprising a compound having a structure according to formula Ia, as defined in claim 13, in combination with a pharmaceutically acceptable carrier to the mammal.

22. A pharmaceutical composition for treating allergic reactions which comprises an anti-allergic effective amount of a compound of formula Ia as defined in claim 13 in combination with a pharmaceutically acceptable carrier.

23. A pharmaceutical composition for treating inflammation which comprises an anti-inflammatory effective amount of a compound of formula Ia as defined in claim 13 in combination with a pharmaceutically acceptable carrier.

24. A pharmaceutical composition for treating peptic ulcers which comprises a cytoprotective effective amount of a compound of formula Ia as defined in claim 13 in combination with a pharmaceutically acceptable carrier.

25. A pharmaceutical composition for treating inflammation which comprises a compound having structural formula I as defined in claim 1 in combination with a pharmaceutically acceptable carrier.

26. A pharmaceutical composition for treating peptic ulcers which comprises a compound having structural formula I as defined in claim 1 in combination with a pharmaceutically acceptable carrier.

27. A method for treating allergic reactions in a mammal which comprises administering an anti-allergic effective amount of the pharmaceutical composition defined in claim 18 to said mammal.

28. A method for treating inflammation in a mammal which comprises administering an anti-inflammatory effective amount of the pharmaceutical composition defined in claim 25 to said mammal.

29. A method of treating peptic ulcers in a mammal which comprises administering a cytoprotective effective amount of the pharmaceutical composition defined in claim 26 to said mammal.

* * * * *